(12) United States Patent
Jin

(10) Patent No.: US 10,195,410 B2
(45) Date of Patent: Feb. 5, 2019

(54) FABRICATION PROCESS OF PHASE-TRANSITION MICRONEEDLE PATCH

(71) Applicant: Tuo Jin, Shanghai (CN)

(72) Inventor: Tuo Jin, Shanghai (CN)

(*) Notice: Subject to any disclaimer, the term of this patent is extended or adjusted under 35 U.S.C. 154(b) by 268 days.

(21) Appl. No.: 14/906,857

(22) PCT Filed: Jul. 22, 2014

(86) PCT No.: PCT/CN2014/082699
§ 371 (c)(1),
(2) Date: Jan. 21, 2016

(87) PCT Pub. No.: WO2015/010599
PCT Pub. Date: Jan. 29, 2015

(65) Prior Publication Data
US 2016/0158511 A1 Jun. 9, 2016

Related U.S. Application Data

(60) Provisional application No. 61/856,767, filed on Jul. 22, 2013.

(51) Int. Cl.
*A61M 37/00* (2006.01)
*B29C 65/00* (2006.01)
(Continued)

(52) U.S. Cl.
CPC ....... *A61M 37/0015* (2013.01); *A61K 9/0021* (2013.01); *B29C 39/026* (2013.01);
(Continued)

(58) Field of Classification Search
None
See application file for complete search history.

(56) References Cited

U.S. PATENT DOCUMENTS

2004/0028875 A1* 2/2004 Van Rijn ............... A61L 27/50
428/98
2011/0270221 A1* 11/2011 Ross ..................... A61B 17/205
604/506
(Continued)

FOREIGN PATENT DOCUMENTS

WO 2008/130587 A2 10/2008
WO 2010/040271 A1 4/2010

OTHER PUBLICATIONS

International Search Report, dated Nov. 13, 2014, for corresponding CN Application No. PCT/CN2014/082699, 3 pages.
(Continued)

*Primary Examiner* — Jeffrey D Washville
(74) *Attorney, Agent, or Firm* — Seed IP Law Group LLP

(57) ABSTRACT

The application discloses a method to fabricate microneedle patches, comprising a) casting (painting and pasting) an aqueous polymer solution on a mold of array of micro-holes which is made of porous materials; b) sucking the polymer solution into the micro-holes by applying vacuum at the back of the mold; d) freezing and thawing the casted polymer solution to induce gelation; and e) drying the gelled polymer solution. Specifically, the present invention describes a process and composition of polymeric microneedlepatch which overcomes the limitations of existing microneedles systems and may be used for transdermal delivery system for therapeutics and other applications.

14 Claims, 2 Drawing Sheets

(51) Int. Cl.
    *B29C 69/00*     (2006.01)
    *B29C 39/02*     (2006.01)
    *B29C 39/42*     (2006.01)
    *A61K 9/00*     (2006.01)
    *B29K 29/00*     (2006.01)
    *B29K 105/00*     (2006.01)
    *B29L 31/00*     (2006.01)

(52) U.S. Cl.
    CPC ............ *B29C 39/42* (2013.01); *B29C 65/002* (2013.01); *B29C 69/00* (2013.01); *A61M 2037/0023* (2013.01); *A61M 2037/0046* (2013.01); *A61M 2037/0053* (2013.01); *B29K 2029/04* (2013.01); *B29K 2105/0035* (2013.01); *B29K 2105/0073* (2013.01); *B29K 2827/18* (2013.01); *B29L 2031/753* (2013.01)

(56) References Cited

U.S. PATENT DOCUMENTS

2014/0066843 A1*   3/2014   Zhang ................. A61K 9/0021
    604/46
2014/0243788 A1*   8/2014   Cantor ............. A61M 37/0015
    604/506

OTHER PUBLICATIONS

Sixing Yang at. al. "A scalable fabrication process of polymer microneedles" International Journal of Nanomedicine, vol. 7, Mar. 9, 2012 (Mar. 9, 2012), ISSN: ISSN 1178-2013, abstract, 1415-1422.

Written Opinion of the International Searching Authority, dated Nov. 13, 2014, for corresponding CN Application No. PCT/CN2014/082699, 4 pages.

* cited by examiner

FABRICATION PROCESS OF PHASE-TRANSITION MICRONEEDLE PATCH

CROSS REFERENCES AND RELATED APPLICATIONS

This application claims priority of U.S. Ser. No. 61/856,767 filed on Jul. 22, 2013, the contents of which are incorporated as reference here into this application.

FIELD OF THE INVENTION

The present invention describes a process and composition of polymeric microneedle patch which overcomes the limitations of existing microneedles systems and may be used for transdermal delivery system for therapeutics and other applications.

BACKGROUND OF THE INVENTION

Non-invasive delivery of protein and peptide therapeutics has been a long-standing objective in pharmaceutical development. Taking diabetes for example, to avoid the lifetime long frequent injection, the scientists in the field have contributed extensive research efforts over half century to examine variety of non-injective methods, comprising the inhalation, oral, nasal spray, needle-free injection, as well as transdermal delivery systems. However, non-injection delivery of protein and peptide medicines across our natural biological barriers remains to be a daunting task.

The invention of microneedles, an array of needles several hundreds micron in length, has provided a promising solution for cross-skin drug delivery. The tiny needles may penetrate the most impermeable layer of skin (stratum corneum) to create diffusion channels for lipophobic molecules without causing skin injury and pain feeling. There are four types of microneedle systems available to date, inorganic solid microneedles, metal hollow microneedles, polymeric dissolvable microneedles, and polymeric swellable microneedles. Among these four systems, only the swellable microneedles are feasible for efficient transdermal delivery of proteins and peptides. Solid microneedles lack a place to load drugs and a diffusion path for loaded drugs to pass through. Although coating medicines on the surface of the needle tips may offer an alternative, the loading capacity is small (approximately 300 ng per needle tip), and moreover, adsorption on metal surface often results in protein denaturing. Metal hollow microneedles, made by deposition of metal vapors onto solid microneedle tamplate, suffer from poor mechanic strength and low production efficiency. Polymeric dissolvable microneedles are actively studied for delivering vaccines, a kind of medication requires limited administration per year. For transdermal delivery of insulin, a drug requiring multiple doses per day, dissolvable microneedles are unflavored for the deposition of needle tips materials in the skin. Swellable microneedles are those which are hard and strong enough to penetrate the epidermis layer at dry state, but convert to swollen by absorbing the body fluid in the dermis layer. Hydration of the matrix of the tips of the swellable microneedles enables proteins or peptide pre-loaded in the microneedles to be released across the epidermis. We name the swellable microneedles as "phase-transition microneedles".

For the microneedles to maintain their shape upon hydration so that they can be withdrawn from the skin without depositing themselves in the skin, the polymeric chains that form the needle matrix must be cross-linked. There are three conceivable mechanisms to cross-link the polymer chains, by covalent bonding, by ionic interaction with multiply charged ions, and by forming nano-crystalline domain as the cross-linking junctions. Covalent bonding method is associated with safety concerns for its involvement of in situ chemical reaction in the presence of medicines after the microneedles are formed. The ionic cross-linking does not create microneedles strong enough to withdraw at hydrated state. In addition, multiply charged ions may also possibly denature proteins. The cross-linking mechanism by formation of nano-crystalline domain is only seen in limited polymeric materials. However, it offers sufficient mechanic strength for the microneedles to complete withdraw from the skin at fully hydrated state. Moreover, the nano-crystalline cross-linking junctions are formed simply by a freeze-thaw treatment, a mild operation to delicate proteins.

This invention demonstrates the structure of a phase-transition microneedle patch and a process to fabricate this microneedle patch by cross-linking the polymer matrix through formation of nano-crystalline domains as the cross-linking junctions.

SUMMARY OF THE INVENTION

The phase-transition microneedle patch in this invention is structured with an array of microneedles loaded with bioactive agents such as drugs and a drug-free supporting plate. The bioactives-loaded microneedle array may include a thin layer of the same polymeric materials loaded with the same drug between the microneedles and the drug-free plate (refer to FIG. 1).

The process to fabricate the microneedle patch involves several steps comprising a) casting (painting and pasting) a drug-loaded aqueous polymer solution on a mold of array of micro-holes which is made of porous materials; b) sucking the viscous polymer solution into the micro-holes by applying vacuum at the back of the mold; c) freezing and thawing the casted polymer solution to induce gelation; and d) drying the gelled polymer solution. To improve the bioavailability of the bioactive agents loaded in the matrix of the microneedles, attaching a pre-made drug-free polymer sheet on the top of the casted microneedles. A solution of the same polymer carrying no bioactive agent may be past on the top of the casted polymer solution as a adhesive to hold the pre-made membrane to microneedles. The freezing and thawing operation may be repeated once or more; and the drying process may be carried out before or after detaching the gelled polymer from the mold. The entire process is described schematically in FIG. 2.

DETAILED DESCRIPTION OF THE INVENTION

Selecting Polymeric Materials

Figure 1:
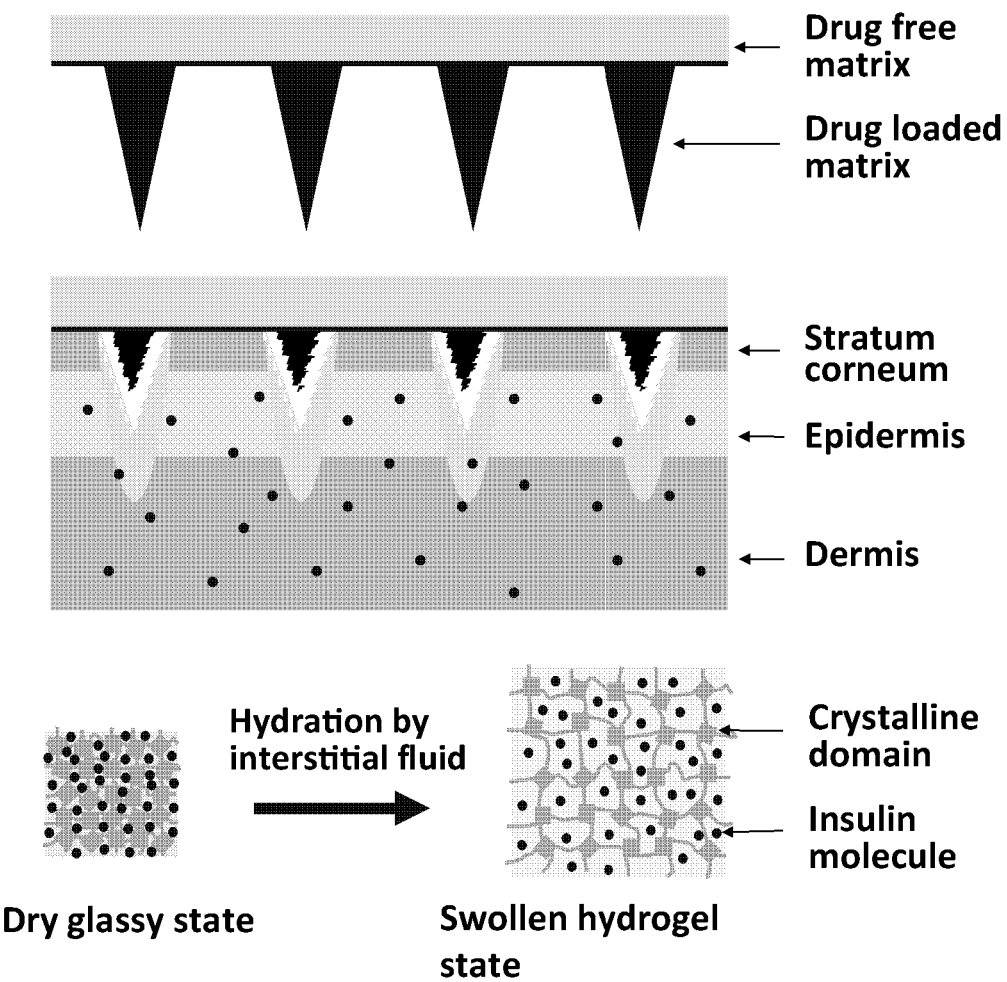
FIG. 1. Schematic illustration of the structure and working mechanism of the phase-transition microneedle patch, wherein majority of the drugs, such as insulin, are loaded in the needle tips, and released by swelling of the needle tips. The swellable but insoluble nature of the matrix of the microneedles is achieved by cross-linking of the polymer chains through micro- or sub-micro-crystalline domains as the cross-linking junctions.
Figure 2:
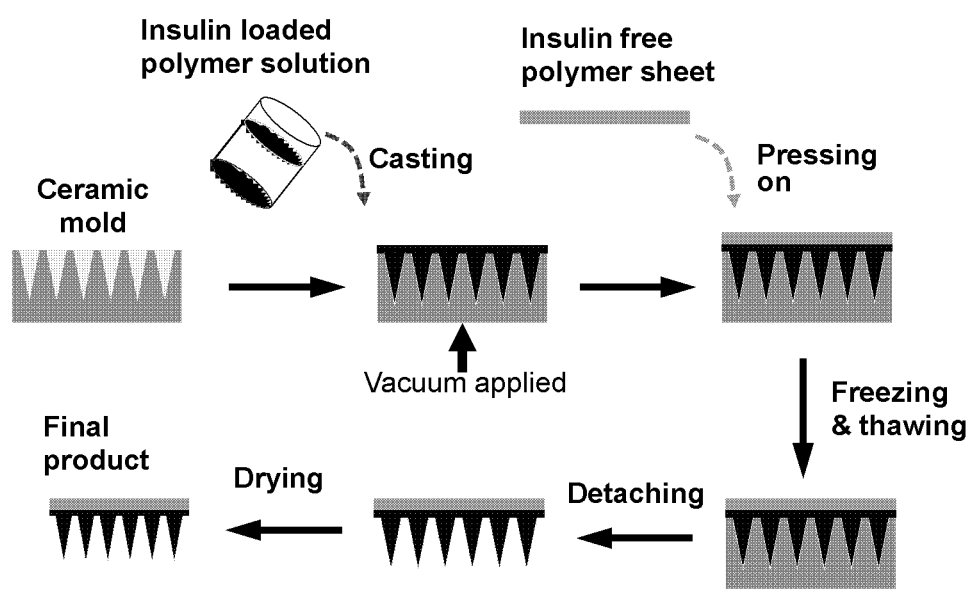
FIG. 2. Schematic description of the process of microneedle fabrication, comprising a) casting a drug-loaded aqueous polymer solution on a mold of array of micro-holes which is made of porous materials; b) socking the viscous polymer solution into the micro-holes by applying vacuum at the back of the mold; c) attaching a pre-made drug-free polymer sheet on the top of the casted microneedles; d) freezing and thawing the casted polymer solution to induce gelation; and e) drying the gelled polymer solution.

Selecting the microneedle-forming polymer or polymers is the first step to prepare phase transition microneedle patch. The polymer must be soluble in water before the patch is formed in order to add the drugs in its aqueous solution and cast on a mold. Then, the microneedle-forming polymeric materials must not be soluble in water after the patch is formed so that the microneedles penetrated skin can retain their shape at hydrated state and be withdrawn completely from the skin after drug administration. Of course, the materials must be hard and strong enough at dry state to penetrate dermis and able to swell when contacting body fluid to open the diffusion channels for drugs.

The materials that meet the above-mentioned criteria are those which are hydrophilic and soluble in water under certain condition (hot water for example) but form water-insoluble hydrogel network hereafter. There are three ways to form hydrogel network, by covalent cross-linking, by ionic interaction, or by forming nano-crystalline domains as the cross-linking junctions. The present invention uses crystallization method, and polymers which may form the nano-crystals by a freeze-thaw treatment at hydrated state comprises polyvinyl alcohol (PVA). The size of the dispersed crystalline domain may vary between nanometers to few microns. The PVA should be over 80% hydrolyzed from polyvinyl acetate.

The polymeric materials used to form the microneedle patch should be compatible to proteins and should better be those used in medication as approved pharmaceutical materials/excipients.

Another important criterion for phase-transition is the permeability of the polymer matrix to the drugs loaded wherein. Protein drugs with molecular weight over 10 KD may be difficult to diffuse through the network of PVA to reach a targeted release rate. In this case, another hydrophilic polymer which does not form the crystalline domains may be blended into the PVA to dilute the density of the nano-crystalline domains. Polysaccharides are a type of ideal materials for this purpose since they are compatible to proteins in general, not forming crystalline structure by the freeze-thaw treatment, and possessing a swelling ratio larger than PVA. The polysaccharide may also improve the hardness of the microneedles and protect the proteins to be loaded as a cryo-protector during the freeze-thaw treatment. The polysaccharides for mixing into PVA are selected from dextran, starch, alginate, carboxyl methyl cellulose, hyaluronic acid and chitosan. In case the mixed polymer solution is too viscous to cast on the mold, the polysaccharides for being added into PVA may be in the form of fine particles each of which is pre-cross-linked. The internally pre-cross-linked polysaccharide particles will dispersed but not dissociate in the PVA solution to make the solution a non-Nuton liquid. For same concentration, a non-Nuton solution will be less viscous than a Nuton solution, so that casting on the mold will be easier.

Designing of Microneedle Patches

The most important factor in designing phase-transition microneedle patch is the location of the drugs. To enable medicines of large molecular weight, such as proteins and large peptides, loading the therapeutic agents only in the matrix of the microneedle tips may greatly improve the efficiency and bioavailability of the transdermal delivery of bioactive agents. For example, for rapid responding to blood sugar, insulin should be loaded in the needle tip part if possible. To concentrate bioactive agents, such as insulin or other large molecules, in the needle tips, the drug-containing polymer solution should all be casted into the micro-holes of the mold. In case some solutions have to be left out of the micro-hold anyway, the layer of the solution on top of the microneedle array must be as thin as possible. If sustained-release function is required, however, this layer may be slightly thicker.

In the case that the bioactive agents need to be concentrated in the microneedle tips, a pre-made hydrogel sheet of the same polymer that contains no bioactive agent may be place on the top of the casted polymer solution containing bioactive agents as a microneedle support. To improve the adhesion of the casted polymer solution containing bioactive agents and the pre-made polymer sheet, an aqueous solution of the same polymer containing no bioactive agents may be pasted as an adhesive prior to pacing the pre-made sheet.

The form of the agent to be delivered may be a factor to manipulate the release rate. For example, the insulin in the form of particles formed with arginine or zinc ions is less soluble than the insulin in free molecule form, and will lead to sustained release.

As a phase-transition microneedle patch, the microneedles are hard at dry state, but swollen at hydrated state. In another word, the microneedles are insoluble in water and maintain their shape at hydrates state. The microneedles should have a length no longer than 2.0 mm.

Design of the Mold

The challenges in designing the casting mold comprise 1) the aqueous polymer solutions for direct casting are much more viscous than monomer solution for post-casting polymerization, and so that much more difficult to full-fill the micro-holes of the mold; 2) in the case that the viscous polymer solution has to be socked into the micro-holes by vacuum, the drugs dissolved in the polymer solution must not be socked away; 3) for massive production, the casted microneedle patch must be detached from the mold easily. To address these issues, the materials for forming the mold must be porous to allow air to pass through, and at the same time, be hydrophobic enough to retain the aqueous solution. The materials should also be less sticky to the polymer solution and/or the hydrogel formed from the solution. Some materials may meet these criteria, for example porous Teflon or Non-sticky porous ceramics.

The Casting Process

To concentrate the drug in the microneedle tips, the drug-loaded aqueous polymer solution for forming the microneedles is first painted on the porous mold which is placed on a vacuum slot. The vacuum slot is connected with a vacuum pump to suck the viscous polymer solution into the micro-holes of the mold made of porous materials. Porous Teflon board is used as a suitable material to form the mold. A scratch board is used to float the painted polymer solution to make it as thin as possible. Then a pre-made PVA hydrogel sheet is placed on the mold to cover the casted polymer solution loaded with drugs. In order to have the casted microneedles to well stand on the PVA sheet, a layer of drug-free PVA solution was paint on top of the drug-loaded solution as the adhesive to glue the microneedles and the pre-made PVA hydrogel sheet together. The thickness of the adhesive PVA solution is between 0.2 to 1.2 mm. The term "drug" here means bioactive agents.

The Drying Process

Drying of the casted microneedle patch may be carried out before or after detaching the patch from the mold. Neither of the cases can easily be achieved due to shrinking of the patch matrix. Drying before detachment of the patch from the mold involves dramatic shrinking of the needle tips. Since the supporting plate does not shrink along the X-Y direction, all the volume loss of the patch by dehydration will be realized in the Z direction, i.e. reduction of the length of the microneedles. Drying after detachment from the mold may offer an even volume shrinking along all the directions theoretically. Shrinking evenly may not only allow the microneedles to maintain their original shape during drying, but also enable technologists to use a mold of larger micro-holes, a criterion greatly easing the mold production. However, absolute even shrinking of non-spherical subject cannot be achieved easily. The microneedle patch will curve it converts from the elastic hydrogel state to the hard glassy state. Therefore, how to prevent curving of the casted microneedle patch during the drying process is highly critical.

We have found that the majority of the volume loss of the patch during the drying process is achieved when it is still in hydrogel state. Curving happens at the last moment before the patch turns itself from hydrogel to glass. By applying a force to limit curving of the sheet of the microneedle patch at the moment when majority of volume loss have been achieved, a straight microneedle plate may be obtained. Based on this finding, we designed a holder to hold the casted microneedle patch to maintain its shape in the last moment of drying. The holder has an edge to press against the sheet of the patch around the area where microneedles stand. The holder should prevent curving of the casted microneedle sheet (before punched to the right sizes) but allow it to shrink at the X-Y directions (the plate level).

Size Determination, Assembly and Packaging

The dried microneedle sheet is punctured to designed sizes, i.e. the patch, determined by the dose of the drug. The back side of the patch of right size will be mounted on an adhesive backing membrane which is impermeable to water vapor. The needle tips side will be covered by a protection sheet which may easily be removed before usage. Finally, the assembled product will be sealed in a moisture-prove bag.

Sterilization

For sterilization, the whole fabrication process of phase-transition microneedle patch may be operated within an aseptic environment, such as under a sterile hood. Sterilization may also be achieved by heating the sealed microneedles to at a temperature between 100-140° C. for certain time period. A reasonable choice may be 110° C. for 15 min.

The invention claimed is:

1. A method to fabricate microneedle patches, comprising:
    a) casting (painting and pasting) an aqueous polymer solution on a mold of array of micro-holes, the mold being made of a plate of porous hydrophobic materials;
    b) sucking the aqueous polymer solution into the micro-holes by applying vacuum at the back of the mold;
    c) freezing and thawing the casted aqueous polymer solution to induce gelation whereby a gelled polymer solution is formed in the mold; and
    d) drying the gelled polymer solution.

2. The method of claim 1, wherein at least one bioactive agent is added in the aqueous polymer solution prior to the casting.

3. The method of claim 1, wherein the mold is permeable to air and the aqueous polymer solution may be sucked into the micro-holes of the mold by applying a vacuum at the back side of the mold.

4. The method of claim 2, wherein a pre-made gelled polymer sheet containing no bioactive agent may be placed as a supporter on the top of the newly casted polymer solution loaded with the bioactive agent.

5. The method of claim 2, wherein a polymer solution free of bioactive agent may be pasted on the top of the casted polymer solution loaded with the bioactive agent as an adhesive prior to placing the pre-made polymer sheet on the top of the casted solutions.

6. The method of claim 1, wherein the drying process may be carried out after detaching the gelled polymer solution in a form of a casted microneedle sheet/patch from the mold.

7. The method of claim 1, wherein the mold is made of a porous Teflon plate.

8. The method of claim 1, wherein after drying, the microneedle sheet/patch is punched to designed sizes.

9. The method of claim 8, wherein microneedle patch of right size is sealed and packed within a moisture-proof bag.

10. The method of claim 1 may be sterilized by including the entire fabrication process within a sterile hood.

11. The method of claim 1, wherein the polymeric material for forming the microneedles is soluble in water and able to form micro- or submicro-crystalline domain as the cross-linking junctions by physical treatment.

12. The method of claim 11 wherein the polymeric material comprises polyvinyl alcohol.

13. The method of claim 12 wherein the polyvinyl alcohol has a degree of hydrolysis of 80% or higher.

14. The method of claim 1, wherein the drying comprises mounting the casted microneedle sheet on a holder to prevent curving of the sheet but allow it to shrink at X-Y (the plate) directions.

* * * * *